United States Patent
Park et al.

(10) Patent No.: US 6,753,443 B1
(45) Date of Patent: Jun. 22, 2004

(54) PREPARING METHOD OF CHIRAL ESTER

(75) Inventors: Jai Wook Park, Pohang-si (KR);
Mahn-Joo Kim, Pohang-si (KR);
Jeong Hwan Koh, Pohang-si (KR);
Hyun Min Jung, Pohang-si (KR)

(73) Assignees: Samsung Fine Chemicals Co., Ltd. (KR); Pohang University of Science and Technology (KR)

( * ) Notice: Subject to any disclaimer, the term of this patent is extended or adjusted under 35 U.S.C. 154(b) by 310 days.

(21) Appl. No.: 09/786,276

(22) PCT Filed: Oct. 18, 2000

(86) PCT No.: PCT/KR00/01170
§ 371 (c)(1),
(2), (4) Date: Mar. 2, 2001

(87) PCT Pub. No.: WO01/28970
PCT Pub. Date: Apr. 26, 2001

(30) Foreign Application Priority Data

Oct. 18, 1999 (KR) ........................................ 1999/45040

(51) Int. Cl.$^7$ ......................... C07C 69/76; C07C 69/74; C07C 69/00; C07C 67/00; C07C 67/02
(52) U.S. Cl. ........................ 560/105; 560/106; 560/108; 560/121; 560/123; 560/124; 560/130; 560/231; 560/254; 560/265
(58) Field of Search ................................. 560/105, 106, 560/108, 121, 123, 124, 130, 231, 254, 265

(56) References Cited

U.S. PATENT DOCUMENTS 5,908,953 A 6/1999 Matsuda et al. ............ 558/441

FOREIGN PATENT DOCUMENTS

| EP | A2-375417 | 6/1990 |
| EP | A1 992481 | 4/2000 |

OTHER PUBLICATIONS

Koh et al, "Efficient Catalytic Racemization of Secondary Alcohols" Tetrahedron Letters, vol. 39, pp. 5545–5548 (1998).*

Koh et al, "Enzymatic resolution of secondary alcohols coupled with ruthenium-catalyzed racemization without hydrogen mediator" Tetrahedron Letters, vol. 40, pp. 6281–6284 (Aug. 20, 1999).*

Mahmoudian et al, "Enzymic Acylation of 506U78 (2–amino–9–beta–D–arabinofuranosyl–6–methoxy–9H– purine), a powerful new anti–leukaemic agent" Biotechnol. Appl. Biochem. vol. 29, pp. 229–233 (Apr. 20, 1999).*

*Ruthenium– and Enzyme–Catalyzed Dynamic Kinetic Resolution of Secondary Alcohols;* J. Am Chem. Soc. 1999, B. Anders Persson, A. L. E. Larsson, M.LeRay and J. E. Backvall, vol. 121, pp. 1645–1650.

*Novel synthetic routes to several new, differentially substituted ruthenium tris (4,4'–disubstituted—2,2–bipyridine) complexes.* Inorganic Chemistry (2000) 39 (2), Dusan Hsek et al.vol. 39, No. 2, Jan. 24, 2000. p. 308–316.

*Ruthenum (II)–Catalyzed Asymmetric Transfer Hydrogenation of Ketones Using a Formic Acid–Triethylamine Mixture;* J. Am Chem. Soc (1996), Fujii, Akio et al., p. 2521–2.

*Catalytic asymmetric and Chemoselective Aerobic oxidation: kinetic resolution of sec–alcohols:* Tetrahedron Letters (2000) 41 (26), Masutani K. et al. pp. 5119–5123.

*Synthesis of ruthenium complexes with planar–chiral cyclopentadienyl–pyridine or –phosphine bidentate ligands;* Royal Society of Chemistry, Noriko Dodo et al., p. 35–41, Dalton (2000).

* cited by examiner

Primary Examiner—Richard L. Raymond
Assistant Examiner—Zachary C. Tucker
(74) Attorney, Agent, or Firm—Finnegan, Henderson, Farabow, Garrett & Dunner, L.L.P.

(57) ABSTRACT

The present invention relates to a process for preparing a chiral ester according to the formula (100):

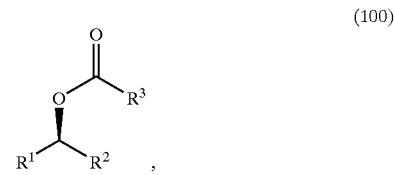

(100)

by reacting (i) a racemic alcohol, (ii) a selected ruthenium complex to activate racemization of the racemic alcohol, (iii) a lipase to selectively acylate one enantiomer of the racemic alcohol, and (iv) an acyl donor compound to supply an acyl group to the lipase.

12 Claims, No Drawings

PREPARING METHOD OF CHIRAL ESTER

This Application was filed under 35 U.S.C. 371 and is the U.S. National Stage of PCT/KR00/01170, filed Oct. 12, 2000.

BACKGROUND OF THE INVENTION

1. Field of the Invention

The present invention relates to a method for preparing a chiral ester and more particularly, the method for preparing an optically pure chiral ester from a racemic alcohol at a high yield.

Recently, studies for using a metal or an enzyme as a catalyst have been increased in asymmetric syntheses. It has been widely known to use an enzyme as a catalyst for kinetic resolution of a racemic mixture in organic syntheses. A variety of effective methods for hydrolysis of an ester and acylation of an alcohol in the presence of lipase as a catalyst has been reported.

Kinetic resolution is the fact that the two enantiomers react at different rates with a chiral addend. An effective kinetic resolution is the enantioselective conversion from a racemic mixture to an optically pure product as shown in scheme 1, leaving the other enantiomer in a reaction medium.

Scheme 1

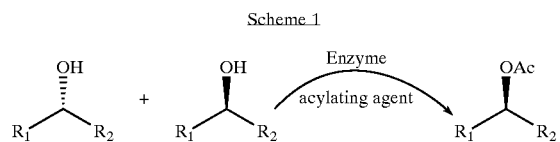

It is well known to prepare a chiral ester from a racemic alcohol by kinetic resolution using esterase. It is possible to obtain an optically pure ester but a maximum yield of this reaction is limited to 50% as shown in scheme 1. Therefore, dynamic kinetic resolution performing kinetic resolution and racemization of an alcohol simultaneously is introduced to resolve such problems (scheme 2).

Scheme 2

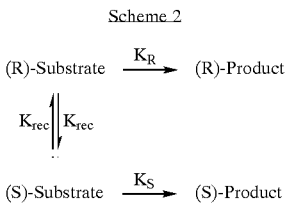

The well-known example of a dynamic kinetic resolution is the reaction by using ruthenium complex expressed in the following structure and lipase (Novozym 435) [B. A. Persson, A. L. E. Larsson, M. L. Ray, and J. E. Backvall, 1. Am. Chem. Soc. 1999,121,1645].

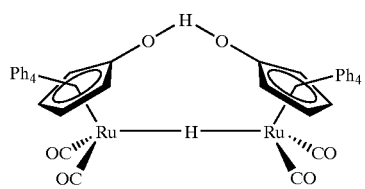

Because racemization of a starting material is performed simultaneously with kinetic resolution, the effectiveness of the starting material is very high and thus, yield of obtaining (R) or (S) enantiomer is theoretically 100%. However, even if the optical purity of a chiral ester obtained by dynamic kinetic resolution is 99 e.e. %, 12 to 40% of ketone as a by-product is produced.

SUMMARY OF THE INVENTION

Therefore, an object of the present invention is to provide a process for preparing an optically pure chiral ester from a racemic alcohol by dynamic kinetic resolution with minimum production of a ketone.

DETAILED DESCRIPTION OF THE INVENTION

A process for preparing a chiral ester of the present invention is characterized by reacting:

a racemic alcohol;

a ruthenium complex selected from the group consisting of compounds 1, 2 and 3 expressed in formulas 1 to 3 to activate racemization of said racemic alcohol;

a lipase to acylate selectively one of enantiomers of said racemic alcohol; and an acyl donor group to supply acyl group to said lipase, (1)

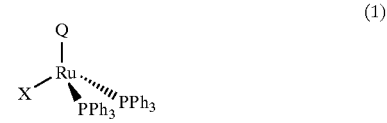

wherein Q is

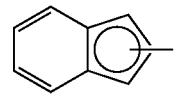

or

and X is Br, Cl or I;

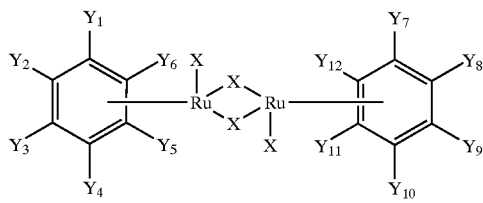

wherein $Y_1$, $Y_2$, $Y_3$, $Y_4$, $Y_5$, $Y_6$, $Y_7$, $Y_8$, $Y_9$, $Y_{10}$, $Y_{11}$, and $Y_{12}$ are independently a hydrogen atom or $C$–$C_5$ alkyl group; and X is Br, Cl or I;

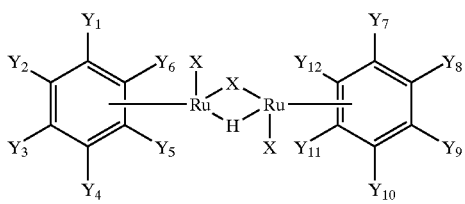

(3)

wherein $Y_1$, $Y_2$, $Y_3$, $Y_4$, $Y_5$, $Y_6$, $Y_7$, $Y_8$, $Y_9$, $Y_{10}$, $Y_{11}$, and $Y_{12}$ are independently a hydrogen atom or $C_1$–$C_5$ alkyl group; and X is Br, Cl or I.

Said ruthenium complex is selected from the group consisting of the compounds 5 to 12 expressed in the following formulas 5 to 12,

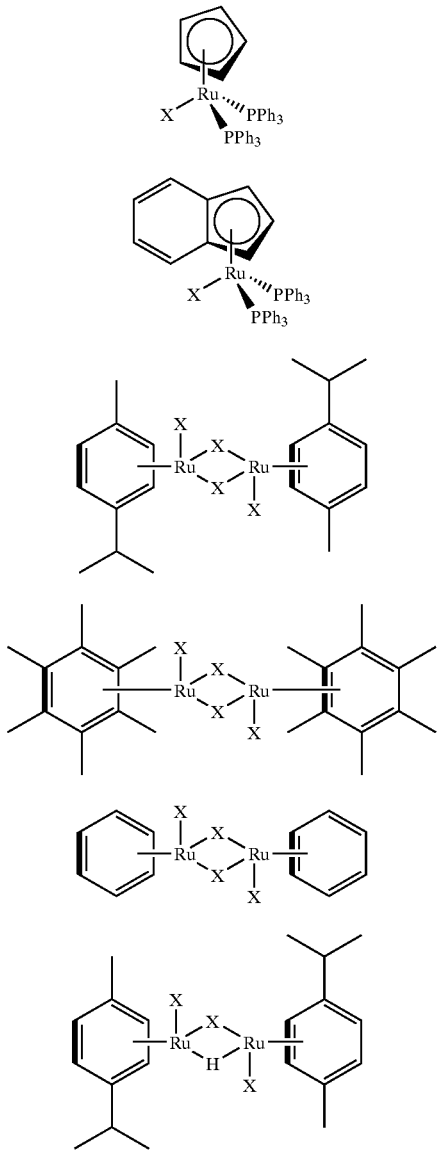

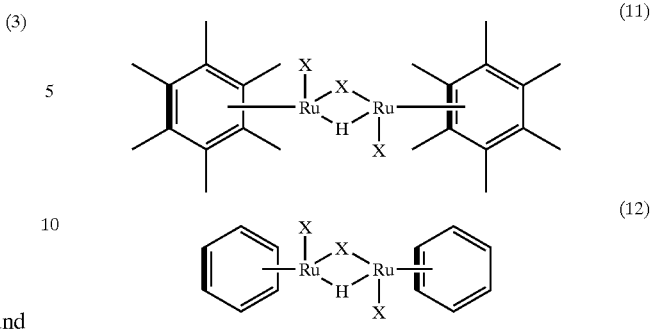

wherein X is Cl, Br or I, the most preferably Cl.

Preferred content of ruthenium complex is 0.1 to 5 mol %, relative to a racemic alcohol. If the content is more than 5 mol %, cost becomes expensive. On the other hand, if it is less than 0.1 mol %, the rate of the reaction becomes too slow.

A method for preparing a chiral ester from a racemic alcohol by dynamic kinetic resolution is described in detail as set forth hereunder.

A mixture of a racemic alcohol, ruthenium complex selected from compounds 1, 2 and 3, lipase and an acyl donor compound is reacted in a solvent in the presence of a base shown in Scheme 3, Scheme 3

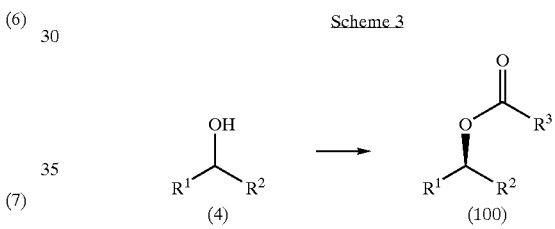

wherein $R^1$, $R^2$ and $R^3$ are, independently, optionally substituted alkyl, optionally substituted aryl or optionally substituted cycloalkyl group and $R^1$ and $R^2$, $R^1$ and $R^3$, and $R^2$ and $R^3$ can be cyclized each other can be cyclized each other, where said substituent of alkyl, aryl and cycloalkyl is a hetero atom such as a halogen atom and a cyano group.

A reaction condition varies with a structure of ruthenium complex. When the ruthenium complex of formula 6 is used, an oxygen gas is required essentially in the reaction and it is performed at a temperature of 40 to 60° C. Said oxygen gas reacts with phosphine, which is a ligand bonded with ruthenium, to convert to phosphine oxide. When the ruthenium complex of formula 7 is used, the reaction is performed at a temperature of 20 to 40° C. When the ruthenium complex of formula 10 is used, the reaction is performed at a temperature of 20 to 40° C. A base is also required to remove acid generated during the reaction. Said base includes triethylamine or diisopropylethyl amine but it is not limited to these examples.

The ruthenium complex of formula 7 is commercially available and is converted to the ruthenium complex of formula 10 in alcohol/base condition. Therefore, results from the ruthenium complex of formula 7 and the ruthenium complex of formula 10 are almost same.

A mechanism of a reaction of a racemic alcohol, ruthenium complex selected from compounds 1, 2 and 3, lipase and an acyl donor compound is described in detail hereunder.

An acyl group supplied from the acyl donor compound is reacted with lipase and this lipase is further reacted with one enantiomer of a racemic alcohol selectively to produce a chiral ester. The other enantiomer is racemized by reacting with ruthenium complex. And further one enantiomer from this racemic alcohol is acylated selectively by lipase and this reaction is repeated to produce optically pure chiral ester with preventing generation of ketone which is a by-product in conventional dynamic kinetic resolution Reaction solvent is not limited but it is preferred to use methylene chloride, toluene, benzene, or hexane because a solvent commonly affects production yield in enzymatic catalysis reaction. An amount of said solvent is used to be 0.2 to 0.3 M concentration of a racemic alcohol.

Said racemic alcohol is generally expressed in the formula 4. It is not limited but examples of the present invention are the following compounds 4a, 5 4b, 4c, 4d, 4e or 4f,

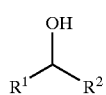
(4)

wherein $R^1$ and $R^2$ are the same as defined above.

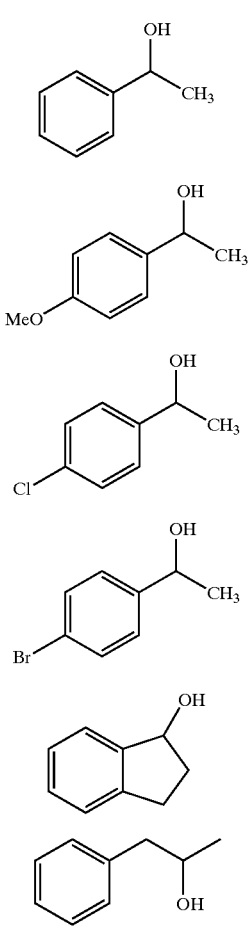

(4a)

(4b)

(4c)

(4d)

(4e)

(4f)

Said lipase, which is esterase, acylates one enantiomer from a racemic alcohol selectively to a chiral ester. Examples of lipase are *Pseuodomonas cepacias* lipase and *Candida antarctica* lipase and more particulary, *Candida antarctica* component B lipase supported on acrylic resin (Novozym 435, Novo company) or *Pseudomonas cepacias* lipase supported on ceramic particle (lipase PS-C, Amano company). An amount of said lipase is in the range of 10 to 60 mg, preferably 30 mg, relative to 1 mmol of an alcohol in Novozym 435 case, and is in the range of 50 to 320 mg, preferably 160 mg, relative to 1 mmol of an alcohol in lipase PS-C case.

Said acyl donor supplies an acyl group to a lipase and acts to move a reaction balance to an acylated product in the presence of a lipase. Preferred acyl donor is aryl ester or alkenyl acetate, the most preferably aryl ester such as p-chlorophenyl acetate having electron withdrawing group. An example of alkenyl acetate is isopropenyl acetate. Such acyl donor compounds are preferred to use because they have an appropriate reactivity without inhibiting racemization. A preferred amount of said acyl donor compound is 2 to 4 equivalents to 1 equivalent of racemic alcohol. If the amount is more than 4 equivalents to 1 equivalent of racemic alcohol, it is difficult to isolate after a reaction. On the other hand, if it is less than 2 equivalents to 1 equivalent of racemic alcohol, the rate of acylation becomes too slow.

A chiral ester expressed in formula 100 is obtained by reacting a racemic alcohol, a ruthenium complex, a lipase, and an acyl donor compound,

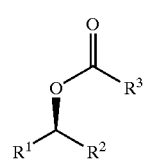
(100)

wherein $R^1$, $R^2$ and $R^3$ are, independently, optionally substituted alkyl, optionally substituted aryl or optionally substituted cycloalkyl group and $R^1$ and $R^2$, $R^1$ and R3, and $R^2$ and $R^3$ can be cyclized each other, where said substituent of alkyl, aryl and cycloalkyl is a hetero atom such as a halogen atom and a cyano group.

The chiral ester of formula 100 of the present invention can be used as a synthetic intermediate for preparing various chiral compounds, chiral pharmaceutical drugs or chiral agrochemicals and more particularly, used as an essential intermediate for preparing Atorvastatin expressed in formula 101 which is a useful drug for treatment for hyperlipemia, L-Carnitine expressed in formula 102 which is as an additive used in food and drugs, and Agenerase expressed in formula 103 which is an essential intermediate of AIDS drug.

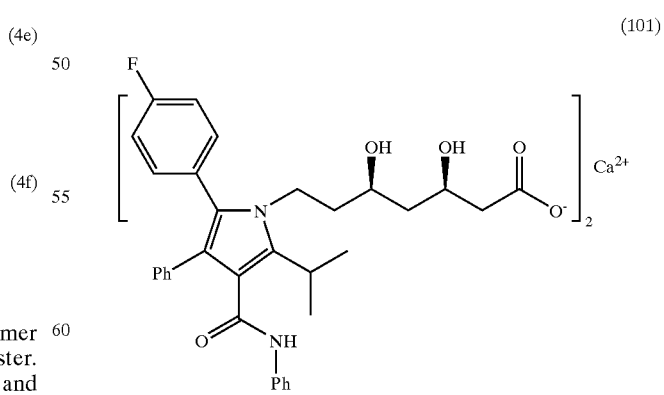

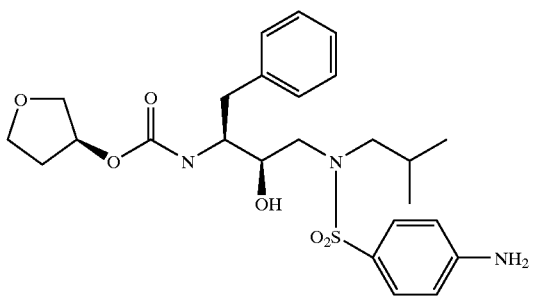

(103)

Especially, a chiral compound of formula 100a which is one of the compounds of the present invention is a key intermediate for preparing Atorvastatin of formula 101 disclosed in U.S. Pat. No. 5,908,953,

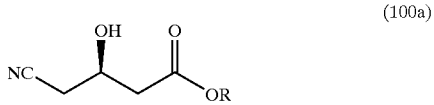

(100a)

wherein R is a low alkyl group.

The process for preparing a chiral ester of formula 100 of the present invention provides minimum production of by-products such as unreacted alcohol residue up to less than 10% and maximum production of product up to 98% having a high optical purity of 99% or more. Because optical purity is the most important factor in preparing chiral compounds for food and pharmaceutical drugs, the chiral ester of the present invention can be used as a useful starting material in various fields, especially fine chemical field.

The following examples are intended to be illustrative of the present invention and should not be construed as limiting the scope of this invention defined by the appended claims.

EXAMPLE 1

A racemic alcohol of formula 4a(0.25 mmol), triethylamine(0.75 mmol), ruthenium complex of formula 6(0.0130 mmol), where X is Cl, 40 mg of lipase PS-C, and p-chlorophenyl acetate (0.75 mmol) were mixed in 2.0 ml of dichloromethane to give a reddish brown suspension.

Argon gas was purged into the reaction suspension, after removing oxygen under the vacuum condition. Oxygen (0.0130 mmol) was injected with syringe in the reaction suspension and then it was heated at 60° C. for 43 hours.

EXAMPLES 2–6

The product, a chiral ester, was prepared by the same procedure of Example 1 except to use racemic alcohol of formulas 4b–4f instead of a racemic alcohol of formula 4a.

EXAMPLE 7

A racemic alcohol of formula 4a(0.25 mmol), triethylamine(0.25 mmol), ruthenium complex of formula 7(0.0130 mmol), where X is Cl, 40 mg of lipase PS-C, and p-chlorophenyl acetate(0.75 mmol) were mixed in 1.2 ml of methylene chloride to give a dark redish suspension.

Argon gas was purged into the reaction suspension, after removing oxygen under the vacuum condition and then it was heated at 40° C. for 44 hours.

EXAMPLES 8–12

The product, chiral ester, was prepared by the same procedure of Example 6 except to use racemic alcohols of formulas 4b–4f instead of a racemic alcohol of formula 4a.

EXAMPLE 13

A racemic alcohol of formula 4a(0.25 mmol), triethylamine(0.25 mmol), ruthenium complex of formula 10(0.0100 mmol), where X is Cl, 40 mg of lipase PS-C, and p-chlorophenyl acetate(0.75 mmol) were mixed in 1.2 ml of methylene chloride to give a dark redish suspension.

Argon gas was purged into the reaction suspension, after removing oxygen under the vacuum condition and then it was heated at 40° C. for 44 hours.

EXAMPLES 14–18

The product, chiral ester, was prepared by the same procedure of Example 11 except to use a racemic alcohol of formulas 4b–4f instead of a racemic alcohol of formula 4a.

Comparative Example 1

A racemic alcohol of formula 4a(2 mmol), ruthenium complex expressed in the following structure below(0.04 mmol), 60 mg of Novozym 435, and p-chlorophenyl acetate(6 mmol) were mixed in 5 ml of toluene to give a dark redish suspension.

The reaction suspension was heated at 70° C. for 46 hours under argon gas.

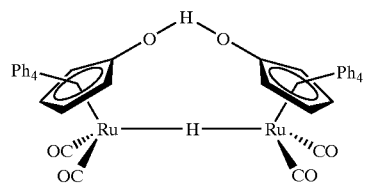

Comparative Examples 2–5

The product, a chiral ester, was prepared by the same procedure of Comparative Example 1 except to use racemic alcohols of formulas 4b, 4d, and 4e and octan-2-ol instead of a racemic alcohol of formula 4a.

Yield, optical purity, and formation of ketone of each reaction of Examples 1–15 and Comparative Examples 1–5 were determined and tabled in Table 1. Said yield was analyzed by $^1$H-NMR spectrum, and said optical purity was determined by high performance liquid chromatography. Said $^1$H-NMR spectrum was taken by using Bruker AM 300 and said high performance liquid chromatography was SpectraSystem P2000.

TABLE 1

| Section | Formation of ketone (%) | Yield (%) | Optical purity (e.e. %) |
| --- | --- | --- | --- |
| Example 1 | 0 | 85 | 96 |
| Example 2 | 0 | 82 | 99 |
| Example 3 | 0 | 98 | 99 |
| Example 4 | 0 | 91 | 95 |
| Example 5 | 0 | 85 | 97 |
| Example 6 | 0 | 92 | 96 |
| Example 7 | 8 | 90 | 94 |
| Example 8 | 10 | 90 | 99 |
| Example 9 | 8 | 90 | 99 |
| Example 10 | 8 | 92 | 99 |
| Example 11 | 8 | 83 | 99 |
| Example 12 | 7 | 91 | 98 |
| Example 13 | 5 | 95 | 94 |
| Example 14 | 7 | 93 | 99 |

TABLE 1-continued

| Section | Formation of ketone (%) | Yield (%) | Optical purity (e.e. %) |
| --- | --- | --- | --- |
| Example 15 | 5 | 93 | 97 |
| Example 16 | 4 | 96 | 99 |
| Example 17 | 4 | 85 | 99 |
| Example 18 | 4 | 95 | 99 |
| Comp. Example 1 | 20 | Below 80 | — |
| Comp. Example 2 | 40 | Below 60 | — |
| Comp. Example 3 | 22 | Below 78 | — |
| Comp. Example 4 | 23 | Below 77 | — |
| Comp. Example 5 | 20 | Below 80 | — |

As shown in Table 1, the amount of a ketone formed as a by-product in Comparative Examples 1 to 5 is in the range of 20 to 40% while that in Examples 1 to 18 is less than 10%. Therefore, the yield of the final product, a chiral ester, prepared by Examples 1 to 18 is much more improved.

As a result, it is proved that the present invention provides a process for preparing an optically pure chiral ester from a racemic alcohol with minimizing the formation of ketone at a high yield in the presence of catalysts which are ruthenium complex selected from formulas 1, 2, and 3, and lipase.

What is claimed is:

1. A process for preparing a chiral ester according to formula (100),

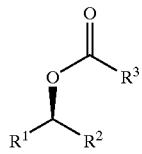

(100)

wherein $R^1$, $R^2$ and $R^3$ are, independently, optionally substituted alkyl, optionally substituted aryl or optionally substituted cycloalkyl group, and wherein $R^1$ and $R^2$ can be cyclized each with other, wherein the process comprises reacting:
  racemic alcohol of formula (4),

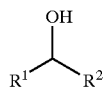

(4)

wherein $R^1$ and $R^2$ are as defined above;
  ruthenium complex selected from the group consisting of compounds 1, 2, and 3 expressed in formulas (1), (2), and (3) to activate racemization of said racemic alcohol wherein:

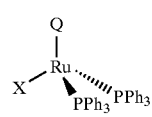

(1)

wherein Q is

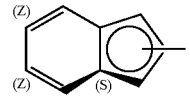

or

and X is Br, Cl or I;

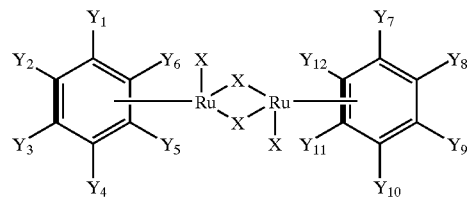

(2)

wherein $Y_1$, $Y_2$, $Y_3$, $Y_4$, $Y_5$, $Y_6$, $Y_7$, $Y_8$, $Y_9$, $Y_{10}$, $Y_{11}$, and $Y_{12}$ are independently a hydrogen atom or $C_1$–$C_5$ alkyl group; and X is Br, Cl or I; and

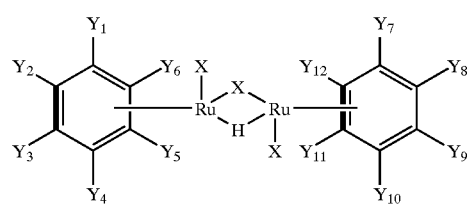

(3)

wherein $Y_1$, $Y_2$, $Y_3$, $Y_4$, $Y_5$, $Y_6$, $Y_7$, $Y_8$, $Y_9$, $Y_{10}$, $Y_{11}$ and $Y_{12}$ are independently a hydrogen atom or $C_1$–$C_5$ alkyl group; and X is Br, Cl or I;

a lipase to acylate one enantiomer selectively from said racemic alcohol; and an acyl donor compound to supply acyl group to said lipase.

2. The process for preparing a chiral ester according to claim 1, wherein said racemic alcohol is selected from the group consisting of compounds 4a, 4b, 4c, 4d, 4e and 4f.

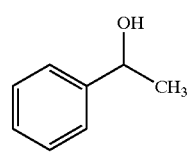

(4a)

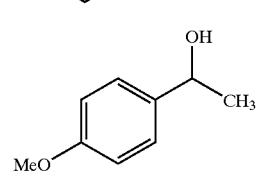

(4b)

(4c)
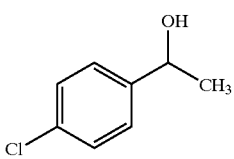

(4d)
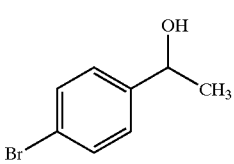

(4e)
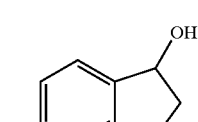

(4f)
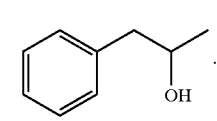

3. The process for preparing a chiral ester according to claim 1, wherein said lipase is selected from the group consisting of *Pseudomonas cepacias* lipase and *Candida antarctica* lipase.

4. The process for preparing a chiral ester according to claim 1, wherein said ruthenium complex is selected from the group consisting of compounds 5, 6, 7, 8, 9, 10, 11 and 12, (5)
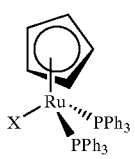

(6)
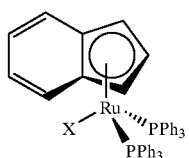

(7)
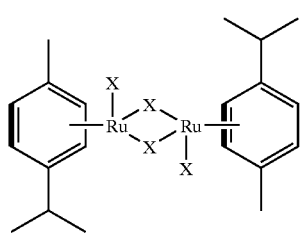

(8)
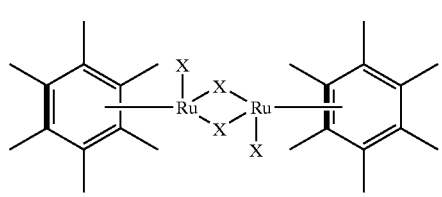

(9)
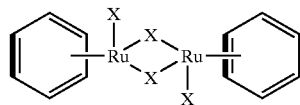

(10)
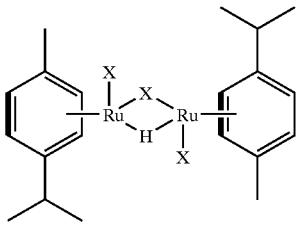

(11)
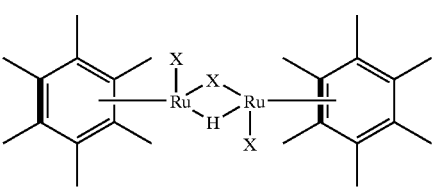

(12)
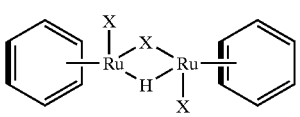

wherein X is Cl, Br or I.

5. The process for preparing a chiral ester according to claim 3, wherein X is Cl.

6. The process for preparing a chiral ester according to claim 1, wherein said reaction requires use of oxygen gas.

7. The process for preparing a chiral ester according to claim 1, wherein a content of said ruthenium complex or its derivatives is in the range of 0.1 to 5 mol % to said racemic alcohol.

8. The process for preparing a chiral ester according to claim 1, wherein said acyl donor compound is selected from an aryl ester.

9. The process for preparing a chiral ester according to claim 8, wherein said aryl ester is selected from p-chlorophenyl acetate.

10. The process according for preparing a chiral ester according to claim 1, wherein the substituent of the alkyl, aryl and cycloalkyl groups are chosen from halogen atoms, and alkoxy and cyano groups.

11. The process for preparing a chiral ester according to claim 1, wherein said acyl donor compound is selected from an alkenyl acetate.

12. The process for preparing a chiral ester according to claim 11, wherein said alkenyl acetate is selected from isopropenyl acetate.

* * * * *

UNITED STATES PATENT AND TRADEMARK OFFICE
CERTIFICATE OF CORRECTION

PATENT NO. : 6,753,443 B1
DATED : June 22, 2004
INVENTOR(S) : Jai Wook Park et al.

It is certified that error appears in the above-identified patent and that said Letters Patent is hereby corrected as shown below:

Title page,
Item [73], Assignee, delete "Samsung Fine Chemicals Co., Ltd. (KR);".

Column 9,
Line 44, "each with other," should read -- with each other, --.
Line 60, "alcohol wherein:" should read -- alcohol, wherein: --.

Column 10,
Line 12, after the structure insert -- ; --.
Line 42, "$Y_{11}$ and" should read -- $Y_{11}$, and --.
Line 52, after "4f" delete ".".

Column 12,
Line 52, after "process" delete "according".

Signed and Sealed this

Thirtieth Day of November, 2004

JON W. DUDAS
*Director of the United States Patent and Trademark Office*